United States Patent
Voegele et al.

(10) Patent No.: US 8,271,086 B2
(45) Date of Patent: *Sep. 18, 2012

(54) PACING OUTPUT DETERMINATION BASED ON SELECTED CAPTURE THRESHOLD VALUES

(75) Inventors: John Voegele, Bethel, MN (US); Clayton Foster, Andover, MN (US); David W. Yost, Brooklyn Park, MN (US); Scott Meyer, Lakeville, MN (US); Yanting Dong, Shoreview, MN (US); Kevin J. Stalsberg, White Bear Lake, MN (US); Derek D. Bohn, Woodbury, MN (US); Eric K. Enrooth, Lino Lakes, MN (US)

(73) Assignee: Cardiac Pacemakers, Inc., Saint Paul, MN (US)

( * ) Notice: Subject to any disclaimer, the term of this patent is extended or adjusted under 35 U.S.C. 154(b) by 855 days.

This patent is subject to a terminal disclaimer.

(21) Appl. No.: 12/341,617

(22) Filed: Dec. 22, 2008

(65) Prior Publication Data

US 2009/0105780 A1    Apr. 23, 2009

Related U.S. Application Data

(63) Continuation of application No. 11/185,573, filed on Jul. 19, 2005, now Pat. No. 7,471,983.

(51) Int. Cl.
*A61N 1/365* (2006.01)
*A61N 1/08* (2006.01)

(52) U.S. Cl. ........................................................ 607/28
(58) Field of Classification Search ............... 607/27–28, 607/11, 17–18
See application file for complete search history.

(56) References Cited

U.S. PATENT DOCUMENTS

| | | | |
|---|---|---|---|
| 6,129,746 | A  | 10/2000 | Levine et al. |
| 6,221,011 | B1 | 4/2001  | Bardy |
| 6,270,457 | B1 | 8/2001  | Bardy |
| 6,277,072 | B1 | 8/2001  | Bardy |
| 6,280,380 | B1 | 8/2001  | Bardy |
| 6,312,378 | B1 | 11/2001 | Bardy |

(Continued)

OTHER PUBLICATIONS

Office Action from U.S. Appl. No. 11/185,573 dated May 7, 2007, 8 pages.
Office Action from U.S. Appl. No. 11/185,573 dated Oct. 29, 2007, 10 pages.
Notice of Allowance dated Aug. 11, 2008 from U.S. Appl. No. 11/185,573, 6 pages.
Office Action Response dated Apr. 4, 2008 from U.S. Appl. No. 11/185,573, 14 pages.
Office Action Response dated Aug. 9, 2007 from U.S. Appl. No. 11/185,573, 9 pages.

*Primary Examiner* — Carl H Layno
*Assistant Examiner* — Jessica Sarcione
(74) *Attorney, Agent, or Firm* — Seager, Tufte & Wickhem, LLC (57) ABSTRACT

Approaches for adjusting the pacing energy delivered by a pacemaker are provided. Adjusting the pacing energy involves performing a plurality of capture threshold tests, each capture threshold test measuring a capture threshold of the heart. One or more measured captured thresholds are selected, including at least one capture threshold that is higher relative to other measured capture thresholds acquired by the plurality of capture threshold tests. The pacing energy is adjusted based on the one or more selected capture thresholds.

20 Claims, 7 Drawing Sheets

U.S. PATENT DOCUMENTS

| | | |
|---|---|---|
| 6,336,903 B1 | 1/2002 | Bardy |
| 6,358,203 B2 | 3/2002 | Bardy |
| 6,368,284 B1 | 4/2002 | Bardy |
| 6,398,728 B1 | 6/2002 | Bardy |
| 6,440,066 B1 | 8/2002 | Bardy |
| 6,512,953 B2 | 1/2003 | Florio et al. |
| 6,587,723 B1 | 7/2003 | Sloman et al. |
| 6,615,082 B1 | 9/2003 | Mandell |
| 6,618,662 B2 | 9/2003 | Schmitt et al. |
| 6,714,819 B1 | 3/2004 | Sloman |
| 6,766,197 B1 | 7/2004 | Levine |
| 7,471,983 B2 * | 12/2008 | Voegele et al. .......... 607/28 |
| 2002/0078968 A1 | 6/2002 | Spinelli et al. |
| 2005/0159785 A1 | 7/2005 | Rueter |

* cited by examiner

PACING OUTPUT DETERMINATION BASED ON SELECTED CAPTURE THRESHOLD VALUES

RELATED PATENT DOCUMENTS

This application is a continuation of U.S. patent application Ser. No. 11/185,573 filed on Jul. 19, 2005, now U.S. Pat. No. 7,471,983, to which Applicant claims priority under 35 U.S.C. §120, and which is incorporated herein by reference in its entirety.

FIELD OF THE INVENTION

The present invention relates generally to medical systems and, more particularly, to adjusting pacing energy of cardiac devices.

BACKGROUND OF THE INVENTION

When functioning normally, the heart produces rhythmic contractions and is capable of pumping blood throughout the body. However, due to disease or injury, the heart rhythm may become irregular resulting in diminished pumping efficiency. Arrhythmia is a general term used to describe heart rhythm irregularities arising from a variety of physical conditions and disease processes. Cardiac rhythm management systems, such as implantable pacemakers and cardiac defibrillators, have been used as an effective treatment for patients with serious arrhythmias. These systems typically comprise circuitry to sense electrical signals from the heart and a pulse generator for delivering electrical stimulation pulses to the heart. Leads extending into the patient's heart are connected to electrodes that contact the myocardium for sensing the heart's electrical signals and for delivering stimulation pulses to the heart in accordance with various therapies for treating the arrhythmias.

Cardiac rhythm management systems operate to stimulate the heart tissue adjacent to the electrodes to produce a contraction of the tissue. Pacemakers are cardiac rhythm management systems that deliver a series of low energy pace pulses timed to assist the heart in producing a contractile rhythm that maintains cardiac pumping efficiency. Pace pulses may be intermittent or continuous, depending on the needs of the patient. There exist a number of categories of pacemaker devices, with various modes for sensing and pacing one or more heart chambers.

When a pace pulse produces a contraction in the heart tissue, the electrical cardiac signal following the contraction is denoted the captured response (CR). The captured response may include an electrical signal, denoted the evoked response signal, associated with the heart contraction, along with a superimposed signal associated with residual post pace polarization at the electrode-tissue interface. The magnitude of the residual post pace polarization signal, or pacing artifact, may be affected by a variety of factors including lead polarization, after-potential from the pace pulse, lead impedance, patient impedance, pace pulse width, and pace pulse amplitude, for example.

A pace pulse must exceed a minimum energy value, or capture threshold, to produce a contraction. It is desirable for a pace pulse to have sufficient energy to stimulate capture of the heart without expending energy significantly in excess of the capture threshold. Thus, accurate determination of the capture threshold is required for efficient pace energy management. If the pace pulse energy is too low, the pace pulses may not reliably produce a contractile response in the heart and may result in ineffective pacing. If the pace pulse energy is too high, the patient may experience discomfort and the battery life of the device will be shorter.

Determination of a capture threshold allows the cardiac rhythm management system to adjust the energy level of pace pulses to correspond to the optimum energy expenditure that reliably produces a contraction. The present invention provides methods and systems for adjusting pacing output energy, and offers numerous advantages over the prior art.

SUMMARY OF THE INVENTION

The present invention involves various methods and systems for adjusting the pacing energy delivered by a pacemaker. In accordance with one embodiment of the invention, a method of adjusting the pacing energy involves performing a plurality of capture threshold tests, each capture threshold test measuring a capture threshold of the heart. One or more measured captured thresholds are selected, including at least one capture threshold that is higher relative to other measured capture thresholds acquired by the plurality of capture threshold tests. The pacing energy is adjusted based on the one or more selected capture thresholds.

In accordance with one aspect of the invention, the plurality of capture threshold tests are performed at predetermined intervals selected to cover the patient's circadian cycle.

One implementation involves selecting the highest capture threshold acquired by the plurality of capture tests and adjusting the pacing energy based on the highest capture threshold. The pacing energy may be adjusted to an energy value that promotes patient safety and device longevity. In one example, the pacing energy is set to about twice the highest capture threshold.

In various implementations, the capture threshold tests may comprise system-initiated or commanded tests. For example, the pacing energy may be initialized based on the capture threshold acquired by a commanded capture threshold test if the commanded test is successful.

According to another aspect of the invention, pacing energy adjustment processes may accommodate operation in several different modes.

Another embodiment of the invention is directed to a pacing energy adjustment system. The pacing energy adjustment system includes capture threshold testing circuitry configured to perform a plurality of capture threshold tests, each capture threshold test measuring a capture threshold of the heart. The system further includes a processor, coupled to the capture threshold testing circuitry. The processor is configured to select at least one measured captured threshold that is higher relative to other measured capture thresholds acquired by the plurality of capture threshold tests. The processor adjusts a pacing energy based on the at least one selected capture threshold. The system includes a memory configured to store capture thresholds acquired by the plurality of capture threshold tests.

According to one aspect of the invention, the processor is configured to operate in several modes including a capture threshold trend only mode and a pacing energy adjust mode.

The processor may be a component of an implantable cardiac rhythm management system. The plurality of capture threshold tests may be initiated by an implantable device. Alternatively, the plurality of capture threshold tests may be initiated by a remote device.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings which form a part hereof, and in which are shown by way of illustration, various embodiments by which the invention may be practiced. It is to be understood that other embodiments may be utilized, and structural and functional changes may be made without departing from the scope of the present invention.

An implantable pacemaker or other cardiac rhythm management (CRM) device may have the capability to determine the capture threshold of one or more heart chambers. Capture threshold testing may be used by the pacemaker or other CRM device to determine a minimum pacing energy required to achieve capture of the chamber or chambers. When the patient's capture threshold value has been measured, the pacing energy may be adjusted to an energy level that is consistent with common practices, patient safety, response to test results, frequency of capture threshold testing, and/or transitions between different threshold test modes. The present invention is directed to methods and systems that use selected capture threshold values to adjust the pacing energy delivered to the heart.

In one example of an automatic capture threshold procedure, the pacemaker delivers a sequence of pacing pulses to the heart and detects the cardiac responses to the pace pulses. The energy of the pacing pulses may be decreased in discrete steps until a predetermined number of loss-of-capture events occur. The pacemaker may increase the stimulation energy in discrete steps until a predetermined number of capture events occur to confirm the capture threshold.

Other procedures for implementing capture threshold testing may be utilized. In one example, the pacing energy may be increased in discrete steps until capture is detected. In another example, the pacing energy may be adjusted according to a binomial search pattern.

Capture threshold testing may be performed using various approaches to determine the cardiac response to pacing. For example, capture threshold testing may employ one or more of the approaches described in commonly owned U.S. Pat. Nos. 7,319,900; 7,337,000; 7,774,064; and 7,574,260, which are incorporated herein by reference.

Figure 1:
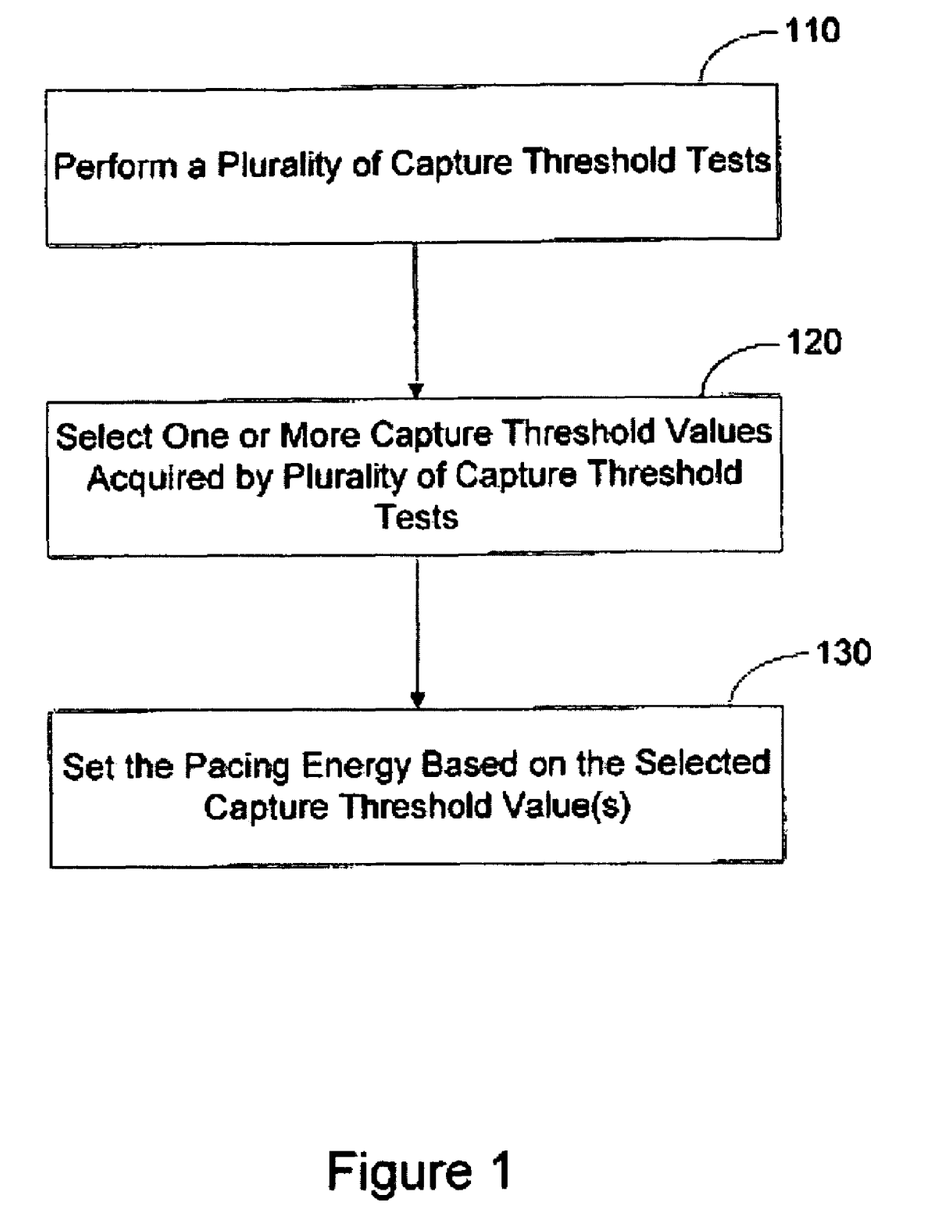
FIG. 1 is a flowchart illustrating a method of adjusting the pacing energy in accordance with embodiments of the invention.

FIG. 1 illustrates pacing energy adjustment in accordance with embodiments of the invention. The pacing energy adjustment may use data acquired from system-initiated and/or commanded capture threshold tests. System-initiated threshold tests may be automatically initiated by the pacemaker or by a remote device communicatively coupled to the pacemaker. System-initiated threshold tests may be set up to occur at predetermined intervals, random intervals, or according to any schedule. Commanded threshold tests refer to tests that are initiated by a physician or other person. For example, the physician may communicate with the pacemaker via a device programmer or other remote system to initiate a capture threshold test.

In accordance with one embodiment, system-initiated capture threshold testing is performed at predetermined intervals that are selected to acquire data throughout a patient's circadian rhythm. For example, capture threshold testing may be scheduled to occur every 21 hours, or according to another time interval.

A plurality of capture threshold tests are performed 110. Capture threshold values acquired by the plurality of capture threshold tests are stored in memory. For example, the memory may comprise a buffer configured to hold a predetermined number of threshold values. In one embodiment, the memory buffer is configured to store about 7 capture threshold values corresponding to about a week of capture threshold tests, where a capture threshold test is performed about every 21 hours. Each newly acquired capture threshold value is stored in the memory buffer and the oldest capture threshold value in the memory buffer is deleted to provide a moving window of capture threshold values. In alternate embodiments, the memory may store more or fewer than 7 capture threshold values.

One or more capture threshold values are selected 120. The selected one or more values are used to adjust 130 the pacing energy delivered to the heart. In accordance with one embodiment, the capture threshold values selected to adjust the pacing energy may comprise one or more capture threshold values that are higher relative to other stored capture threshold values. The selected capture threshold values may be processed in various ways before setting the pacing energy. For example, the selected higher capture threshold values may be used to compute an average value or weighted average value, and the pacing energy may be adjusted based on the average or weighted average value.

In accordance with another embodiment, the highest capture threshold value may be selected and used to adjust the pacing energy. The pacing energy may be set to the selected capture threshold value (or average value of more than one selected value) plus a safety margin. In one implementation, the pacing energy may be set to the selected capture threshold value or the value computed from multiple selected capture threshold values plus a safety offset. In another implementation, the pacing energy may be set equal to a multiple of the selected values or average value. In one embodiment, the pacing energy is set to about twice the highest value of the stored capture threshold values.

The approaches of the present invention may be implemented to adjust the pacing energy such that a satisfactory pacing safety margin is maintained. For example, adjusting the pacing energy to twice the capture threshold value provides a 100% safety margin. Further, the pacing energy adjustment may be performed within a range of values to provide pacing energy output that conforms to pacing device capabilities and common practices. For example, a minimum pacing energy level that is consistent with common practices may be used, e.g., about 2 V. A maximum pacing energy level that is consistent with the intended uses of the pacing device may be used, e.g., about 5 V.

The approaches of the present invention may be used to account for circadian variation of the patient's capture threshold. In addition, elevations in capture threshold level are responded to relatively quickly whereas decreases in capture threshold levels are cautiously approached to maintain patient safety.

Figure 2:
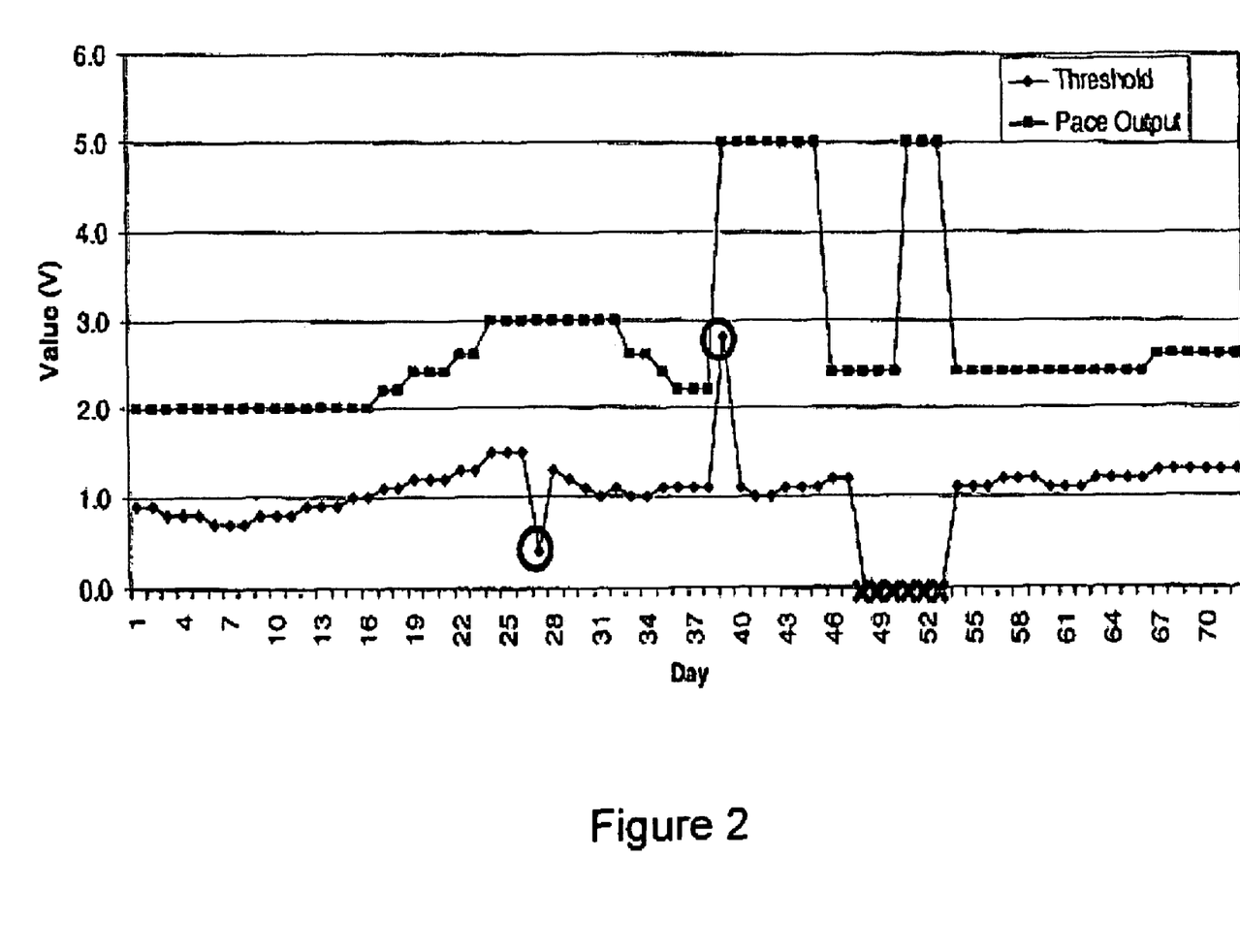
FIG. 2 illustrates graphs comparing measured capture thresholds to pacing energy adjusted in accordance with embodiments of the invention.

FIG. 2 is a graph illustrating selection of capture threshold values for pacing energy adjustment in accordance with embodiments of the invention. In the example illustrated by FIG. 2, the pacing energy is set to twice the highest capture threshold value determined in the past seven days with a 2 V minimum limit and a 5 V maximum default value. FIG. 2 shows a graph of measured capture threshold values and a graph of pacing output energies over a 72 day period. As can be seen in FIG. 2, the pacing energy during days 1-16 is set to the minimum pacing output value, which in this example is 2 V, because the measured capture threshold values remain below 1 V during this period. On day 17, capture threshold testing acquires a pacing threshold value above 1 V and the pacing energy is adjusted above the 2 V minimum on day 17.

Comparison of the graphs of measured capture thresholds and pacing output energies during days 17-26 show that the pacing output energy tracks increases in capture threshold. On day 27, an unusually low capture threshold is measured. The pacing output does not track this unusually low capture threshold measurement and responds cautiously to a decreasing trend of capture threshold measurements acquired during days 27-38. On day 38, a capture threshold value greater than 2.5 V is measured. The system responds by setting the pacing output to the default value, which in this example is 5 V. Pacing at the default value is maintained for 7 days, until the capture threshold value measured on day 38 is deleted from the moving window of stored capture threshold values.

On days 48-53, the capture threshold testing is unsuccessful. After four consecutive unsuccessful capture threshold tests, on day 51, the system responds by setting the pacing output to the default value. Although this example responds after four consecutive unsuccessful capture threshold test events, any number may be used. The pacing output energy is maintained at the default value until a successful capture threshold test is performed on day 54. The system then continues to track the highest capture threshold measured within the moving window of the most recent 7 successful tests.

Figure 3:
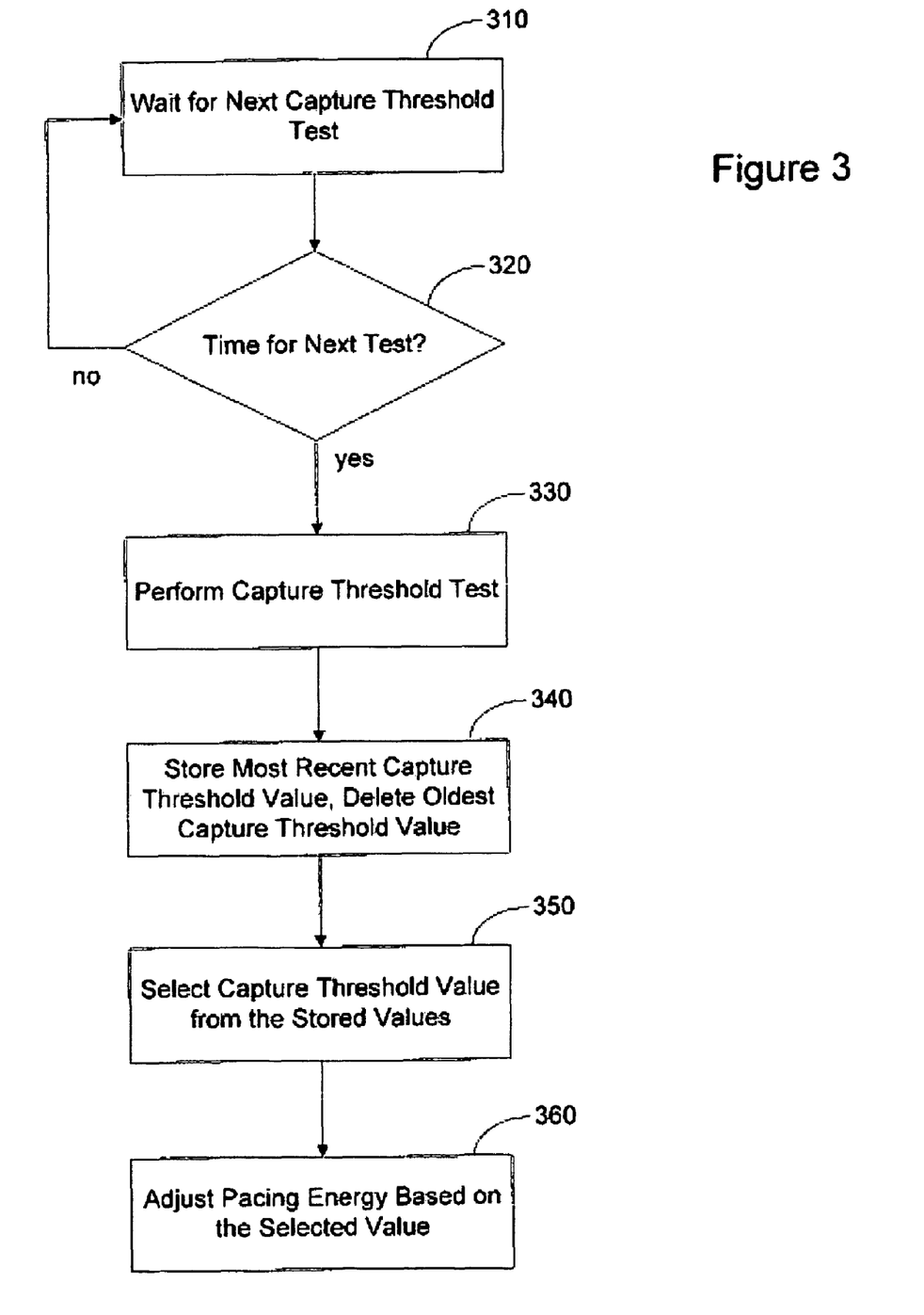
FIG. 3 is a flowchart illustrating a method of adjusting the pacing energy in accordance with embodiments of the invention.

FIG. 3 is a flowchart illustrating a method of adjusting the pacing energy in accordance with embodiments of the invention. The system performs 330 a capture threshold test periodically 310, 320, such as once every 24 hours, once every 21 hours, at random intervals, or according to some other schedule. The measured capture threshold values are stored in memory. The data is stored so that a moving window of capture threshold measurements are maintained, wherein the most recent capture threshold measurement replaces 340 the oldest capture threshold measurement. If there are less than 7 successful test results stored in the moving window, all test results are retained. One or more capture threshold measurements are selected 350 from the stored values and are used 360 to adjust the pacing output.

For example, the moving window may store the test results from the last seven (or other number of) successful daily tests and the pacing energy may be adjusted based on the highest capture threshold value from the last seven threshold tests. If seven threshold values are not available, then as many as are available may be used. The default pacing value, e.g., 5V, may be used until a capture threshold test is successfully performed. If a predetermined number of successive capture threshold tests are unsuccessful, the system may flag this and set the pacing energy output to the default value until a capture threshold test is successfully performed.

The seven day moving window, with capture threshold testing performed every 21 hours, for example, provides protection for variations in capture threshold levels due to circadian changes. Furthermore, the risk of one erroneously low measurement affecting the pacing output energy and putting the patient in danger is reduced. Although a single erroneous high measurement may increase the pacing level for several days, this does not significantly impact device longevity.

The system may accommodate both system-initiated capture threshold testing and commanded capture threshold tests. A system-initiated capture threshold test may be initiated, for example, by an implantable device, such as a cardiac pacemaker. Alternatively, the system-initiated capture threshold tests may be initiated by a patient-external system, such as advanced patient management (APM) system in communication with the implantable pacemaker. The advanced patient management system may be used to automatically initiate tests, and also allows physicians or other personnel to remotely initiate tests and/or monitor patient conditions. In one example, a cardiac pacemaker, defibrillator, or other device, may be equipped with various telecommunications and information technologies that enable real-time data collection, diagnosis, and treatment of the patient. Various embodiments described herein may be used in connection with advanced patient management. Methods, structures, and/or techniques described herein, which may be adapted to provide for remote patient/device monitoring, diagnosis, therapy, or other APM related methodologies, may incorporate features of one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference.

Figure 4:
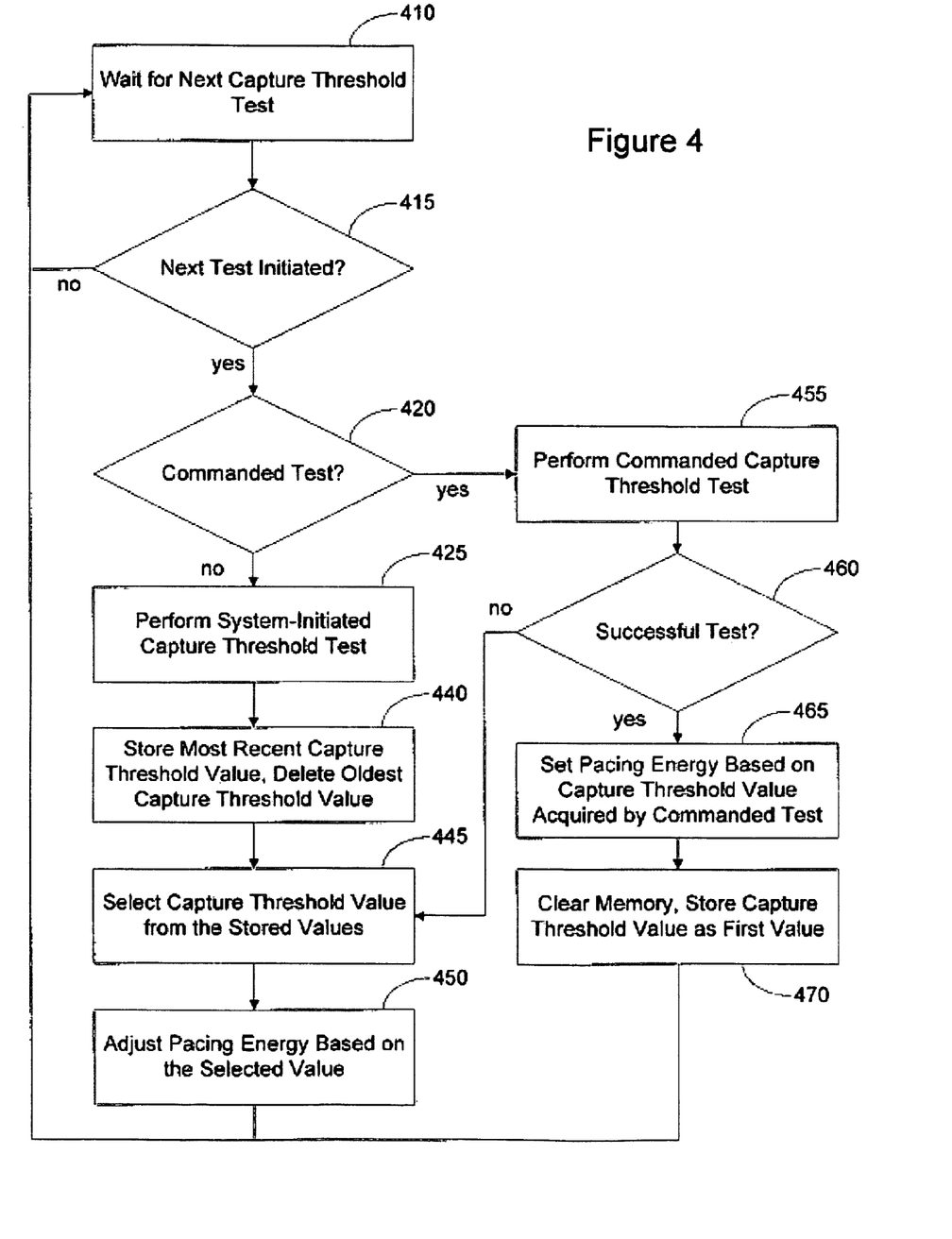
FIG. 4 illustrates a method of initializing the pacing energy based on results of a commanded threshold test in accordance with embodiments of the invention.

Capture threshold tests may be performed on command, for example, by a physician or other person communicating with the implantable pacemaker via a device programmer or APM system. The system's response to system-initiated capture threshold tests may be different from the system's response to commanded tests. FIG. 4 is a flow chart illustrating a method of adjusting pacing output in accordance with embodiments of the invention when both system-initiated and commanded threshold tests may be performed. The system initially waits 410 for a capture threshold test to be initiated 415. If the capture threshold test is system-initiated 420, the threshold test is performed 425 and the acquired capture threshold measurement is stored 440 in the moving window storage. The highest capture threshold value is selected 445 from the stored capture threshold values and is used to adjust 450 the pacing output.

If the initiated capture threshold test is 420 a commanded test, e.g., initiated by a physician or other person, then the system performs 455 the commanded test. If the patient's capture threshold is successfully measured 460, then the pacing energy is based 465 on the capture threshold value acquired by the commanded test. The moving window of threshold values stored in memory is cleared 470 and the capture threshold value acquired by the commanded threshold test is stored as the first value in the moving window. This process avoids the confusion that would occur during a follow up if the pacing output after a commanded test did not agree with the measurement acquired during the commanded test as expected.

The pacemaker may have the capability of operating in several different modes. For example, the pacemaker may operate in an "OFF" mode, wherein system-initiated capture threshold testing is not performed. The pacemaker may operate in an "ON" mode, where system-initiated capture threshold testing is performed and selected capture threshold values are used to adjust the pacing output. The pacemaker may also operate in a "TREND" mode, wherein system-initiated capture threshold testing is performed and the acquired capture threshold values are stored, however, the pacing energy is not adjusted.

Figure 5:
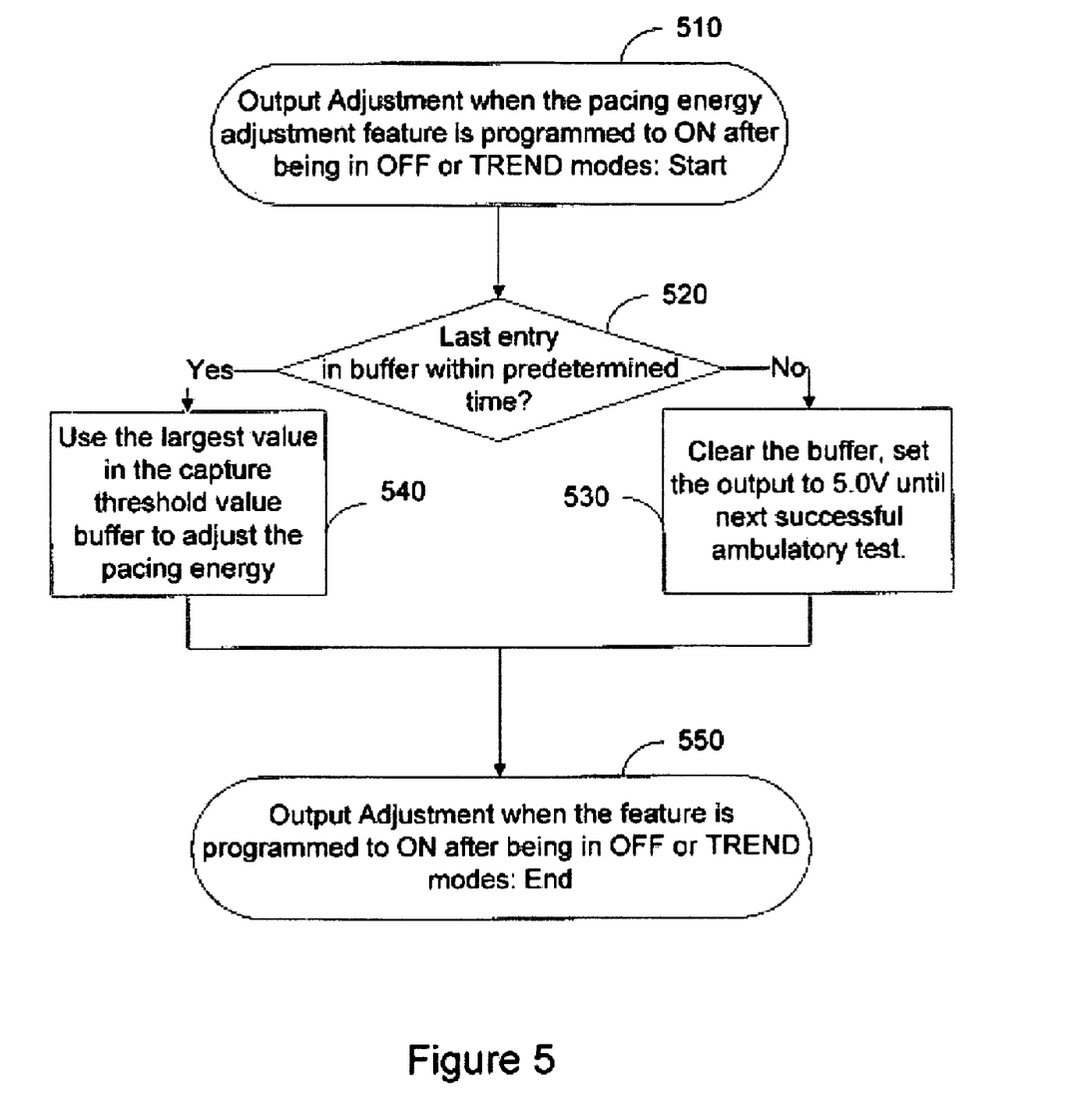
FIG. 5 illustrates pacing energy adjustment when the pacing energy adjustment mode is switched to "ON" mode from "Trend" or "Off" modes in accordance with embodiments of the invention.

The flowchart of FIG. 5 illustrates pacing energy output adjustment 510 when the mode is switched to ON from TREND or OFF. The illustrated approach provides for appropriately utilizing information from previous commanded and trend-only capture threshold tests.

If there is at least one capture threshold value in the moving window buffer that was acquired 520 during a predetermined time interval, e.g., 21 hours, prior to the mode switch, the pacing output is adjusted 540 based on the highest stored capture threshold value. The moving window buffer may be configured to store about 7 capture threshold values, for example.

If there is no capture threshold value in the moving window buffer that was acquired 520 during the predetermined time interval, the moving window memory buffer is cleared 530 and the pacing energy is set to the default value, e.g. 5V, until the next successful capture threshold test is performed. The result of the next capture threshold test may be applied immediately.

The timing of the next system-initiated test is determined by the entry point into the 21 hour (or other time value) test interval. For example, assuming a 21 hour test interval, the next system-initiated capture threshold test may occur anywhere between 1 hour to 22 hours from the time the system is switched to ON mode. After the pacing output energy adjustment following 550 the mode switch to the ON mode, pacing energy adjustment may continue according to the methods illustrated in the flowcharts of FIG. 3 or FIG. 4.

Figure 6:
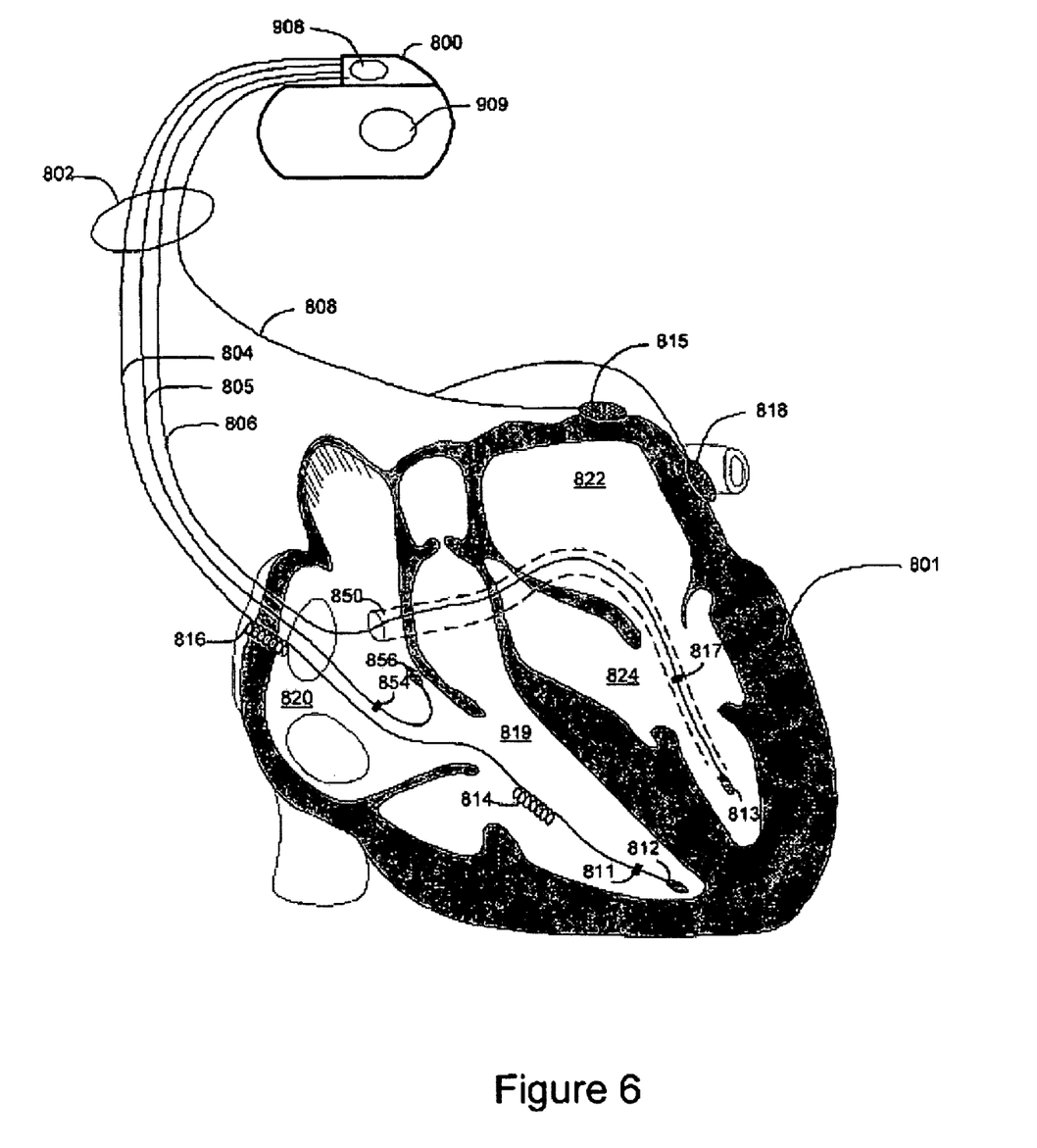
FIG. 6 illustrates a cardiac rhythm management system that may be used to implement pacing energy adjustment in accordance with embodiments of the invention.

Referring now to FIG. 6 of the drawings, there is shown a cardiac rhythm management system that may be used to implement pacing energy adjustment in accordance with the present invention. The cardiac rhythm management system illustrated in FIG. 6 includes a pacemaker/defibrillator 800 electrically and physically coupled to a lead system 802. The housing and/or header of the pacemaker/defibrillator 800 may incorporate one or more electrodes 908, 909 used to provide electrical stimulation energy to the heart and to sense cardiac electrical activity. The pacemaker/defibrillator 800 may utilize all or a portion of the pacemaker/defibrillator housing as a can electrode 909. The pacemaker/defibrillator 800 may include an indifferent electrode 908 positioned, for example, on the header or the housing of the pacemaker/defibrillator 800. If the pacemaker/defibrillator 800 includes both a can electrode 909 and an indifferent electrode 908, the electrodes 908, 909 typically are electrically isolated from each other.

The lead system 802 is used to detect electric cardiac signals produced by the heart 801 and to provide electrical energy to the heart 801 under certain predetermined conditions to treat cardiac arrhythmias. The lead system 802 may include one or more electrodes used for pacing, sensing, and/or defibrillation. In the embodiment shown in FIG. 6, the lead system 802 includes an intracardiac right ventricular (RV) lead system 804, an intracardiac right atrial (RA) lead system 805, an intracardiac left ventricular (LV) lead system 806, and an extracardiac left atrial (LA) lead system 808. The lead system 802 of FIG. 6 illustrates one embodiment that may be used in connection with the pacing output determination methodologies described herein. Other leads and/or electrodes may additionally or alternatively be used.

The lead system 802 may include intracardiac leads 804, 805, 806 implanted in a human body with portions of the intracardiac leads 804, 805, 806 inserted into a heart 801. The intracardiac leads 804, 805, 806 include various electrodes positionable within the heart for sensing electrical activity of the heart and for delivering electrical stimulation energy to the heart, for example, pacing pulses and/or defibrillation shocks to treat various arrhythmias of the heart.

As illustrated in FIG. 6, the lead system 802 may include one or more extracardiac leads 808 having electrodes, e.g., epicardial electrodes, positioned at locations outside the heart for sensing and pacing one or more heart chambers.

The right ventricular lead system 804 illustrated in FIG. 6 includes an SVC-coil 816, an RV-coil 814, an RV-ring electrode 811, and an RV-tip electrode 812. The right ventricular lead system 804 extends through the right atrium 820 and into the right ventricle 819. In particular, the RV-tip electrode 812, RV-ring electrode 811, and RV-coil electrode 814 are positioned at appropriate locations within the right ventricle 819 for sensing and delivering electrical stimulation pulses to the heart 801. The SVC-coil 816 is positioned at an appropriate location within the right atrium chamber 820 of the heart 801 or a major vein leading to the right atrial chamber 820 of the heart 801.

In one configuration, the RV-tip electrode 812 referenced to the can electrode 909 may be used to implement unipolar pacing and/or sensing in the right ventricle 819. Bipolar pacing and/or sensing in the right ventricle may be implemented using the RV-tip 812 and RV-ring 811 electrodes. In yet another configuration, the RV-ring 811 electrode may optionally be omitted, and bipolar pacing and/or sensing may be accomplished using the RV-tip electrode 812 and the RV-coil 814, for example. The RV-coil 814 and the SVC-coil 816 are defibrillation electrodes.

The left ventricular lead 806 includes an LV distal electrode 813 and an LV proximal electrode 817 located at appropriate locations in or about the left ventricle 824 for pacing and/or sensing the left ventricle 824. The left ventricular lead 806 may be guided into the right atrium 820 of the heart via the superior vena cava. From the right atrium 820, the left ventricular lead 806 may be deployed into the coronary sinus ostium, the opening of the coronary sinus 850. The lead 806 may be guided through the coronary sinus 850 to a coronary vein of the left ventricle 824. This vein is used as an access pathway for leads to reach the surfaces of the left ventricle 824 which are not directly accessible from the right side of the heart. Lead placement for the left ventricular lead 806 may be achieved via subclavian vein access and a preformed guiding catheter for insertion of the LV electrodes 813, 817 adjacent to the left ventricle.

Unipolar pacing and/or sensing in the left ventricle may be implemented, for example, using the LV distal electrode referenced to the can electrode 909. The LV distal electrode 813 and the LV proximal electrode 817 may be used together as bipolar sense and/or pace electrodes for the left ventricle. The left ventricular lead 806 and the right ventricular lead 804, in conjunction with the pacemaker/defibrillator 800, may be used to provide cardiac resynchronization therapy such that the ventricles of the heart are paced substantially simultaneously, or in phased sequence, to provide enhanced cardiac pumping efficiency for patients suffering from chronic heart failure.

The right atrial lead 805 includes a RA-tip electrode 856 and an RA-ring electrode 854 positioned at appropriate locations in the right atrium 820 for sensing and pacing the right atrium 820. In one configuration, the RA-tip 856 referenced to the can electrode 909, for example, may be used to provide unipolar pacing and/or sensing in the right atrium 820. In another configuration, the RA-tip electrode 856 and the RA-ring electrode 854 may be used to provide bipolar pacing and/or sensing.

FIG. 6 illustrates one embodiment of a left atrial lead system 808. In this example, the left atrial lead 808 is implemented as an extracardiac lead with LA distal 818 and LA proximal 815 electrodes positioned at appropriate locations outside the heart 801 for sensing and pacing the left atrium 822. Unipolar pacing and/or sensing of the left atrium may be accomplished, for example, using the LA distal electrode 818 to the can 909 pacing vector. The LA proximal 815 and LA distal 818 electrodes may be used together to implement bipolar pacing and/or sensing of the left atrium 822.

Figure 7:
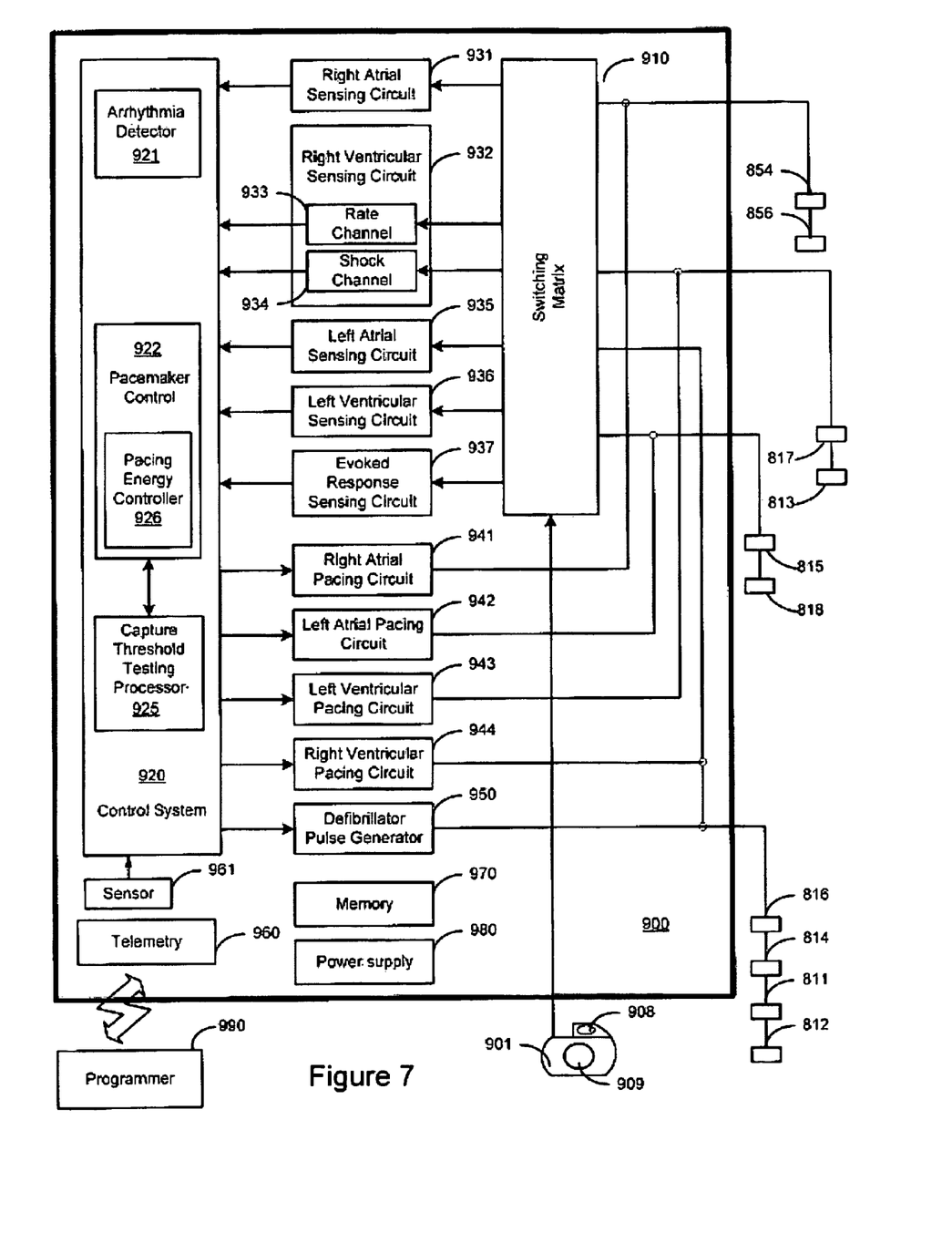
FIG. 7 is block diagram of a cardiac pacemaker/defibrillator suitable for implementing pacing energy adjustment methods of the present invention.

Referring now to FIG. 7, there is shown a block diagram of a cardiac pacemaker/defibrillator 900 suitable for implementing pacing energy adjustment methods of the present invention. FIG. 7 shows a cardiac pacemaker/defibrillator 900 divided into functional blocks. It is understood by those skilled in the art that there exist many possible configurations in which these functional blocks can be arranged. The example depicted in FIG. 7 is one possible functional arrangement. Other arrangements are also possible. For example, more, fewer or different functional blocks may be used to describe a cardiac pacemaker/defibrillator suitable for implementing the methodologies for pacing output determination in accordance with the present invention. In addition, although the cardiac pacemaker/defibrillator 900 depicted in FIG. 7 contemplates the use of a programmable microprocessor-based logic circuit, other circuit implementations may be utilized.

The cardiac pacemaker/defibrillator 900 depicted in FIG. 7 includes circuitry for receiving cardiac signals from a heart and delivering electrical stimulation energy to the heart in the form of pacing pulses or defibrillation shocks. In one embodiment, the circuitry of the cardiac pacemaker/defibrillator 900 is encased and hermetically sealed in a housing 901 suitable for implanting in a human body. Power to the cardiac pacemaker/defibrillator 900 is supplied by an electrochemical battery 980. A connector block (not shown) is attached to the housing 901 of the cardiac pacemaker/defibrillator 900 to allow for the physical and electrical attachment of the lead system conductors to the circuitry of the cardiac pacemaker/defibrillator 900.

The cardiac pacemaker/defibrillator 900 may be a programmable microprocessor-based system, including a control system 920 and a memory 970. The memory 970 provides the moving window buffer for storing capture threshold values and may also store parameters for various pacing, defibrillation, and sensing modes, along with other parameters. The memory 970 may be used, for example, for storing historical EGM and therapy data. The historical data storage may include, for example, data obtained from long-term patient monitoring used for trending and/or other diagnostic purposes. Historical data, as well as other information, may be transmitted to an external programmer unit 990 as needed or desired.

The control system 920 and memory 970 may cooperate with other components of the cardiac pacemaker/defibrillator 900 to control the operations of the cardiac pacemaker/defibrillator 900. The control system depicted in FIG. 7 incorporates a capture threshold testing processor 925 for performing capture threshold tests to acquire the patient's capture threshold. The control system also includes a pacing energy controller 926. The control system adjusts the pacing energy based on capture threshold values acquired by the threshold testing processor in accordance with embodiments of the invention. The control system 920 includes additional functional components including a pacemaker control circuit 922, and may include an arrhythmia detector 921, along with other components for controlling the operations of the cardiac pacemaker/defibrillator 900.

Telemetry circuitry 960 may be implemented to provide communications between the cardiac pacemaker/defibrillator 900 and an external programmer unit 990 or other remote system. In one embodiment, the telemetry circuitry 960 and the programmer unit 990 communicate using a wire loop antenna and a radio frequency telemetric link, as is known in the art, to receive and transmit signals and data between the programmer unit 990 and the telemetry circuitry 960. In this manner, commands, such as commands relating to threshold testing, may be transferred to the control system 920 of the cardiac pacemaker/defibrillator 900 from the programmer unit 990 during and after implant. In addition, stored cardiac data, e.g., pertaining to capture threshold values, along with other data, may be transferred to the programmer unit 990 from the cardiac pacemaker/defibrillator 900. The telemetry circuitry 960 may provide for communication between the cardiac pacemaker/defibrillator 900 and an APM system as previously described.

In the embodiment of the cardiac pacemaker/defibrillator 900 illustrated in FIG. 7, electrodes RA-tip 856, RA-ring 854, RV-tip 812, RV-ring 811, RV-coil 814, SVC-coil 816, LV distal electrode 813, LV proximal electrode 817, LA distal electrode 818, LA proximal electrode 815, indifferent electrode 908, and can electrode 909 are coupled through a switch matrix 910 to sensing circuits 931-937.

A right atrial sensing circuit 931 serves to detect and amplify electrical signals from the right atrium of the heart. Bipolar sensing in the right atrium may be implemented, for example, by sensing voltages developed between the RA-tip 856 and the RA-ring 854. Unipolar sensing may be implemented, for example, by sensing voltages developed between the RA-tip 856 and the can electrode 909. Outputs from the right atrial sensing circuit are coupled to the control system 920.

A right ventricular sensing circuit 932 serves to detect and amplify electrical signals from the right ventricle of the heart. The right ventricular sensing circuit 932 may include, for example, a right ventricular rate channel 933 and a right ventricular shock channel 934. Right ventricular cardiac signals sensed through use of the RV-tip 812 electrode are right ventricular near-field signals and are denoted RV rate channel signals. A bipolar RV rate channel signal may be sensed as a voltage developed between the RV-tip 812 and the RV-ring 811. Alternatively, bipolar sensing in the right ventricle may be implemented using the RV-tip electrode 812 and the RV-coil 814. Unipolar rate channel sensing in the right ventricle may be implemented, for example, by sensing voltages developed between the RV-tip 812 and the can electrode 909.

Right ventricular cardiac signals sensed through use of the defibrillation electrodes are far-field signals, also referred to as RV morphology or RV shock channel signals. More particularly, a right ventricular shock channel signal may be detected as a voltage developed between the RV-coil 814 and the SVC-coil 816. A right ventricular shock channel signal may also be detected as a voltage developed between the RV-coil 814 and the can electrode 909. In another configuration the can electrode 909 and the SVC-coil electrode 816 may be electrically shorted and a RV shock channel signal may be detected as the voltage developed between the RV-coil 814 and the can electrode 909/SVC-coil 816 combination.

Left atrial cardiac signals may be sensed through the use of one or more left atrial electrodes 815, 818, which may be configured as epicardial electrodes. A left atrial sensing circuit 935 serves to detect and amplify electrical signals from the left atrium of the heart. Bipolar sensing and/or pacing in the left atrium may be implemented, for example, using the LA distal electrode 818 and the LA proximal electrode 815. Unipolar sensing and/or pacing of the left atrium may be accomplished, for example, using the LA distal electrode 818 to can vector 909 or the LA proximal electrode 815 to can vector 909.

A left ventricular sensing circuit 936 serves to detect and amplify electrical signals from the left ventricle of the heart. Bipolar sensing in the left ventricle may be implemented, for example, by sensing voltages developed between the LV distal electrode 813 and the LV proximal electrode 817. Unipolar sensing may be implemented, for example, by sensing voltages developed between the LV distal electrode 813 or the LV proximal electrode 817 and the can electrode 909.

Optionally, an LV coil electrode (not shown) may be inserted into the patient's cardiac vasculature, e.g., the coronary sinus, adjacent the left heart. Signals detected using combinations of the LV electrodes, 813, 817, LV coil electrode (not shown), and/or can electrodes 909 may be sensed and amplified by the left ventricular sensing circuitry 936. The output of the left ventricular sensing circuit 936 is coupled to the control system 920.

The outputs of the switching matrix 910 may be operated to couple selected combinations of electrodes 811, 812, 813, 814, 815, 816, 817, 818, 856, 854 to an evoked response sensing circuit 937. The evoked response sensing circuit 937 serves to sense and amplify voltages developed using various combinations of electrodes for discrimination of various cardiac responses to pacing in accordance with embodiments of the invention. The capture threshold testing processor 925 may analyze the output of the evoked response sensing circuit 937 to acquire capture threshold values. The results of the capture threshold testing may be used by the pacing energy controller 926 to adjust the pacing energy.

Various combinations of pacing and sensing electrodes may be utilized in connection with pacing and sensing the cardiac signal following the pace pulse to classify the cardiac response to the pacing pulse. For example, in some embodiments, a first electrode combination is used for pacing a heart chamber and a second electrode combination is used to sense the cardiac signal following pacing. In other embodiments, the same electrode combination is used for pacing and sensing.

The pacemaker control circuit 922, in combination with pacing circuitry for the left atrium, right atrium, left ventricle, and right ventricle 941, 942, 943, 944, may be implemented to selectively generate and deliver pacing pulses to the heart using various electrode combinations. The pacing electrode combinations may be used to effect bipolar or unipolar pacing pulses to a heart chamber using one of the pacing vectors as described above. In some implementations, the cardiac pacemaker/defibrillator 900 may include a sensor 961 that is used to sense the patient's hemodynamic need. The timing of the pacing pulses may be adjusted to respond to the patient's hemodynamic need based on the sensor 961 output.

Various modifications and additions can be made to the embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method of operating a cardiac device to adjust a pacing energy delivered to a heart, comprising:
  performing a plurality of capture threshold tests that respectively measure a plurality of capture thresholds of the heart;
  decreasing the pacing energy in response to measuring two or more capture thresholds of the plurality of measured capture thresholds that are less than a value used to set a current pacing energy; and
  increasing the pacing energy in response to measuring at least one capture threshold of the plurality of measured capture thresholds that is greater than the value used to set the current pacing energy.

2. The method of claim 1, wherein:
  performing the plurality of capture threshold tests comprises performing the plurality of capture threshold tests at predetermined intervals over about one week; and
  storing the plurality of capture threshold tests in a moving window buffer.

3. The method of claim 1, wherein increasing the pacing energy comprises increasing the pacing energy to a highest capture threshold measured by the plurality of capture threshold tests plus a safety margin.

4. The method of claim 1, further comprising adjusting the pacing energy to a predetermined value if at least two of the capture threshold tests are unsuccessful.

5. The method of claim 4, further comprising reducing the pacing energy based on a capture threshold measured by a successful capture threshold test performed after the pacing energy is adjusted to the predetermined value.

6. The method of claim 1, performing the plurality of capture threshold tests comprises performing the plurality of capture threshold tests at intervals that cover the patient's circadian cycle.

7. The method of claim 1, wherein the plurality of capture threshold tests comprises a plurality of system-initiated capture threshold tests.

8. The method of claim 7, further comprising:
  storing capture thresholds acquired by the plurality of system-initiated capture threshold tests;
  performing a capture threshold test commanded by a physician; and
  clearing the stored capture thresholds and storing a capture threshold measured by the commanded capture threshold test if the commanded capture threshold test is successful.

9. The method of claim 8, further comprising adjusting the pacing energy based on the capture threshold measured by the commanded capture threshold test.

10. The method of claim 1, further comprising storing the plurality of capture thresholds in a moving window buffer.

11. The method of claim 1, further comprising:
adjusting the pacing energy based on a stored capture threshold value acquired during a predetermined time interval occurring prior to switching to a pacing energy adjustment mode; and
setting the pacing energy to a default value if there is no stored capture threshold value acquired during the predetermined time interval.

12. A pacing energy adjustment system, comprising:
cardiac electrodes electrically coupled to a heart;
capture threshold testing circuitry configured to perform a plurality of capture threshold tests to measure a plurality of capture thresholds; and
a processor, coupled to the capture threshold testing circuitry, the processor configured to decrease the pacing energy in response to measuring two or more capture thresholds of the plurality of measured capture thresholds that are less than a value used to set a current pacing energy and to increase the pacing energy in response to measuring at least one capture threshold of the plurality of measured capture thresholds that is greater than the value used to set the current pacing energy.

13. The system of claim 12, wherein the plurality of capture threshold tests are performed at time intervals selected to cover a patient's circadian cycle.

14. The system of claim 12, wherein the processor is configured to operate in several modes including a capture threshold trend mode and a pacing energy adjust mode.

15. The system of claim 12, wherein the processor is configured to set the pacing energy to a default value if two or more capture threshold tests of the plurality of capture threshold tests are unsuccessful.

16. The system of claim 12, further comprising a moving window buffer configured to store a predetermined number of capture thresholds measured by the plurality of capture threshold tests.

17. The system of claim 16, wherein the moving window buffer is configured to store capture thresholds taken at multiple points of the patient's circadian cycle during a period of about one week.

18. The system of claim 16, wherein the processor is configured to adjust the pacing energy based on a capture threshold acquired by a capture threshold test commanded by a physician and to erase the moving window buffer.

19. The system of claim 12, wherein the processor is a component of an implantable device, and the plurality of capture threshold tests are initiated by the implantable device.

20. The system of claim 12, wherein the processor is a component of an implantable device, and the system further comprises a remote device communicatively coupled to the implantable device, and the plurality of capture threshold tests are initiated by the remote device.

* * * * *